US009791371B2

(12) United States Patent
York et al.

(10) Patent No.: US 9,791,371 B2
(45) Date of Patent: Oct. 17, 2017

(54) SYSTEMS AND METHODS FOR DISTINGUISHING STIMULATED EMISSIONS AS A MEANS OF INCREASING THE SIGNAL OF FLUORESCENCE MICROSCOPY

(71) Applicant: The United States of America, as Represented by Secretary, Department of Health and Human Services, Washington, DC (US)

(72) Inventors: Andrew York, Rockville, MD (US); Sanjay Varma, Rockville, MD (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 14/927,263

(22) Filed: Oct. 29, 2015

(65) Prior Publication Data
US 2016/0123887 A1    May 5, 2016

Related U.S. Application Data

(60) Provisional application No. 62/072,218, filed on Oct. 29, 2014.

(51) Int. Cl.
*G02B 21/06* (2006.01)
*G01N 21/64* (2006.01)
*G02B 21/16* (2006.01)

(52) U.S. Cl.
CPC ......... *G01N 21/6458* (2013.01); *G02B 21/06* (2013.01); *G02B 21/16* (2013.01); *G01N 2201/06113* (2013.01)

(58) Field of Classification Search
CPC .......................... G02B 21/00; G02B 21/0004; G02B 21/0076; G02B 21/06; G02B 21/16; G01J 3/28; G01J 3/44; G01J 3/4406; G01J 3/4412; G01N 21/62; G01N 21/63; G01N 21/64; G01N 21/65
USPC ....... 359/362, 363, 368, 369, 385, 389, 390; 356/416, 417, 420, 301, 317, 318
See application file for complete search history.

(56) References Cited

U.S. PATENT DOCUMENTS

| 5,731,588 A * | 3/1998 | Hell ........................ G01N 21/63 |
| | | 250/458.1 |
| 2010/0252750 A1* | 10/2010 | Xie ........................ G01N 21/636 |
| | | 250/459.1 |
| 2013/0201552 A1* | 8/2013 | Sander ................ G02B 21/0076 |
| | | 359/385 |

OTHER PUBLICATIONS

L. Wei, W. Min, 'What can stimulated emission do for bioimaging?', Ann. N.Y. Acad. Sci., 2013, pp. 1-7.*
W. Min, S. Lu, S. Chong, R. Roy, G. R. Holtom, X. S. Xie, 'Imaging chromophores with undetectable fluorescence by stimulated emission microscopy', Nature, vol. 461, Oct. 22, 2009, pp. 1105-1109.*

* cited by examiner

*Primary Examiner* — Arnel C Lavarias
(74) *Attorney, Agent, or Firm* — Polsinelli PC

(57) ABSTRACT

Embodiments of a fluorescence microscopy system that employs a technique for distinguishing stimulated emission as a means for enhancing signal strength of fluorescent markers are disclosed.

17 Claims, 2 Drawing Sheets

SYSTEMS AND METHODS FOR DISTINGUISHING STIMULATED EMISSIONS AS A MEANS OF INCREASING THE SIGNAL OF FLUORESCENCE MICROSCOPY

CROSS REFERENCE TO RELATED APPLICATIONS

This is a non-provisional application that claims benefit to U.S. provisional patent application Ser. No. 62/072,218, filed on Oct. 29, 2014, which is incorporated by reference in its entirety.

FIELD

The present document generally relates to fluorescence microscopy and in particular to systems and methods of distinguishing stimulated emissions as a means of increasing the signal from fluorophores.

BACKGROUND

Fluorescence microscopy is an invaluable tool for biologists, which provides high-resolution, high-speed, protein-specific imaging in living cells, tissues, and animals. In particular, fluorescence microscopy uses markers which absorb light and spontaneously re-emit that light at a different wavelength. The nanosecond-scale lag between absorption and spontaneous emission limits how much light a fluorescent marker emits per second, which fundamentally limits measurement speed and precision. For example, seeing individual steps of a RNA polymerase as it moves along a DNA strand requires a fluorescent marker which emits thousands of photons per millisecond, much more than typical fluorescent proteins can produce. As such, greatly increasing the brightness and photostability of fluorescent markers would enable high speed, high precision measurements which are currently impossible.

Spontaneous emission is not the only way for an excited marker to emit light after absorption. If an excited marker is illuminated with light of the proper color, it can also be "stimulated" to emit. Since the rate of stimulated emission can be much faster than spontaneous emission, stimulated emission can be several orders of magnitude brighter than spontaneous emission, an exciting possibility for improving fluorescent marker brightness. However, stimulated emission is difficult to distinguish from the stimulating light—it is the same color, the same phase, the same polarization, and, in bulk materials, goes the same direction. Noise and background from the stimulating beam is therefore difficult to reject, which negates the advantage of stimulated emission for increasing marker brightness. As such, no method to cleanly distinguish stimulated emission from the stimulating beam is currently known.

SUMMARY

In one embodiment, a fluorescence microscopy system includes an excitation source for generating an excitation light beam along a first axis and a stimulation source for generating a stimulation light beam along a second axis that is in perpendicular orientation relative to the first axis, wherein the excitation light beam and the stimulation light beam have different wavelengths. In addition, a sample having one or more fluorescent markers is provided which may be illuminated by the excitation light beam such that the one or more fluorescent markers assume an excited state and then illuminated again by the stimulation light beam to generate a stimulated emission by the initially excited sample. An objective lens is oriented along the second axis for capturing and focusing the stimulation light beam and stimulated emission emitted by the one or more fluorescent markers. A stimulation light beam block component is positioned at the focal point of the objective lens such that the stimulation light beam is blocked while allowing the stimulated emission to pass. Finally, a detector is provided for detecting the stimulated emission.

In another embodiment, a method for fluorescence microscopy includes illuminating one or more fluorescent markers in a sample with an excitation light beam from an excitation source oriented along a first axis such that the one or more fluorescent marker assume an excited state; illuminating the one or more fluorescent markers in the excited state with a stimulation light beam from a stimulation source oriented along a second axis that is in perpendicular relation to the first axis, wherein a stimulated emission is generated by the one or more fluorescent markers when illuminated by the stimulation light beam, and wherein the stimulated light beam and the excitation light beam have different wavelengths; focusing the stimulation light beam and the stimulated emission through an objective lens; positioning a stimulated light beam block component along the second axis such that the stimulated light beam is focused onto and blocked by the stimulated light beam block component, and wherein the stimulated emission is not blocked by the positioning of the stimulated light beam block; and detecting the stimulated emission by a detector.

In yet another embodiment, a fluorescence microscopy system includes an excitation source for generating an excitation light beam along a first axis and a stimulation source for generating a stimulation light beam along a second axis that is in perpendicular relation relative to the first axis, wherein the excitation light beam and the stimulation light beam have different wavelengths. A combined excitation/stimulation light beam is generated by the intersection of the excitation light beam with the stimulation light beam with an excitation objective lens oriented along the first axis for capturing the combined excitation/stimulation light beam. A sample having one or more fluorescent markers is provided in the focal plane of the excitation objective lens, wherein the one or more fluorescent markers are illuminated by the combined excitation/stimulation light beam for producing a stimulated emission. In addition, a detection objective lens is oriented in perpendicular orientation relative to the excitation objective for capturing and focusing the stimulated emission emitted by the one or more fluorescent markers of the sample and a detector for detecting the stimulated emission from the detection objective lens.

In a further embodiment, a method for fluorescence microscopy includes generating an excitation light beam along a first axis; generating a stimulation light beam along a second axis that is in perpendicular orientation relative to the first axis, wherein the excitation light beam and the stimulation light beam have different wavelengths; intersecting the excitation light beam with the stimulation light beam such that a combined excitation/stimulation light beam is generated and directed along the second axis focusing the combined excitation/stimulation light beam through an excitation objective oriented along the second axis onto a sample having one or more fluorescent markers such that the one or more fluorescent markers are illuminated by the combined excitation/stimulation light beam and emit a stimulated emission; focusing the stimulated emission through a detection objective lens oriented along a third axis that is in perpendicular relation relative to the second axis and in parallel relation relative to the first axis; and detecting the stimulated emission with a detector.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
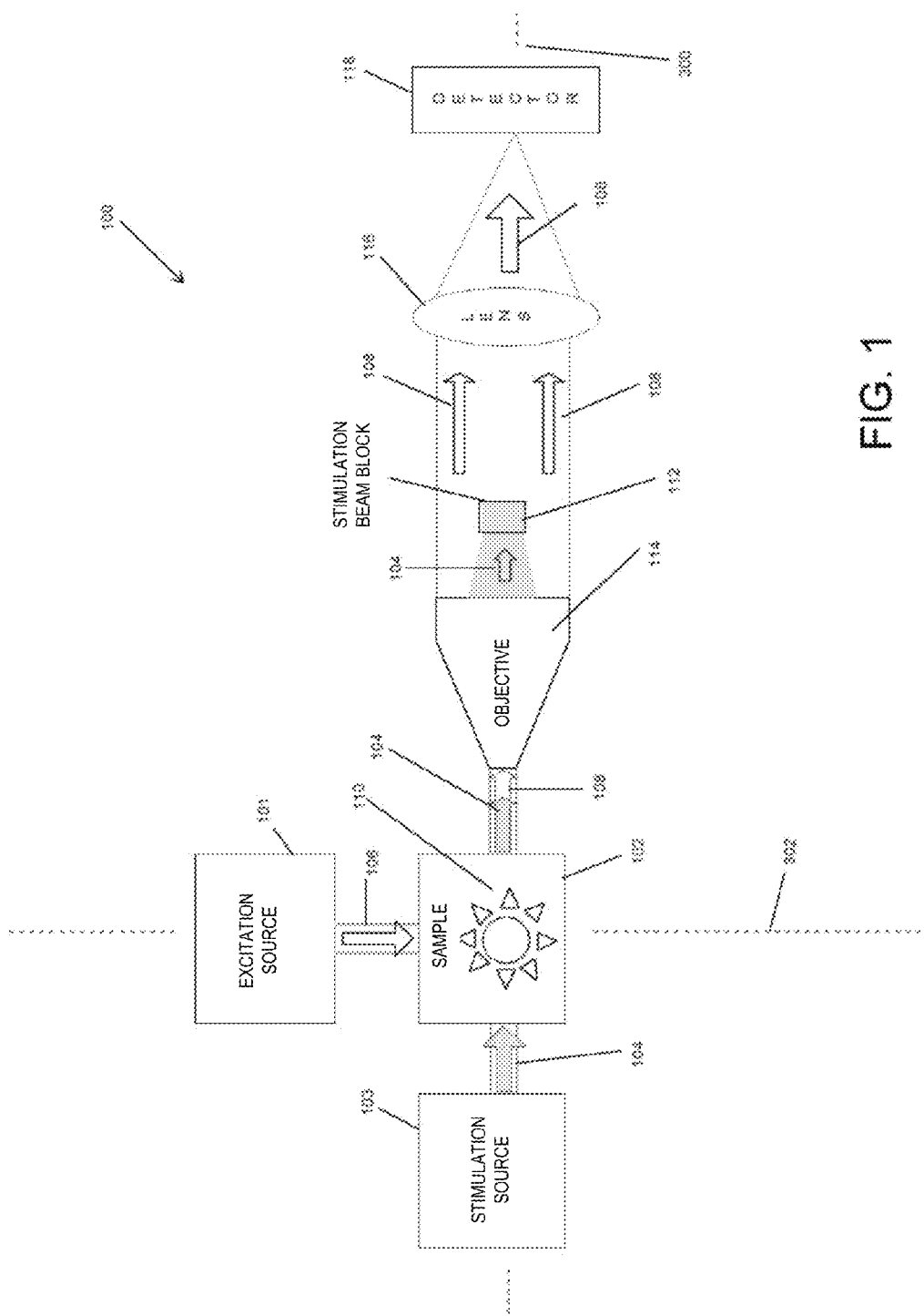
FIG. 1 is a simplified illustration of one embodiment of a fluorescence microscopy system.

Various embodiments of a fluorescence microscopy system that employs a technique for distinguishing stimulated emission as a means of enhancing signal strength of fluorescent markers for detection are disclosed. Referring to the drawings, embodiments of a fluorescence microscopy system are illustrated and generally indicated as 100 and 200 in FIGS. 1 and 2.

As shown in FIG. 1, one embodiment of a fluorescent microscopy system 100 that employs one technique for distinguishing stimulated emission as a means of enhancing signal strength of fluorescent markers is shown. In one arrangement, an excitation beam 106 is used to illuminate a sample 102 along an axis 302 in which one or more fluorescent molecules 110 (e.g. fluorescent markers) associated with the sample 102 are excited by the excitation light beam 106. For example, the excitation light beam 106 may be generated by an excitation source 101, such as a laser, that emits a single light beam having a wavelength of about 488 nm.

Once the fluorescent molecules 110 assume an excited state after illumination by the excitation light beam 106, a stimulation light beam 104 is then used to illuminate the sample 102 along an axis 300 that is in perpendicular relation to the axis 302 of the excitation light beam 106. In some embodiments, the stimulation light beam 104 may be generated by a stimulation source 103, such as a laser, in which the stimulation light beam 104 comprises collimated light having a wavelength of about 550 nm or any other wavelength that is different than the wavelength of the excitation light beam 106. In some embodiments, the stimulation light beam 104 may be focused onto the sample 102 using an optics arrangement (not shown) to illuminate the excited fluorescent molecules 110 immediately after initial excitation occurs in the sample 102 by the excitation light beam 106. It was discovered that if the excited fluorescent molecules 110 are illuminated once again with light of the proper wavelength (e.g., stimulation light beam 104) after initial excitation, the excited fluorescent molecules 110 will be stimulated to emit a stimulated emission 108 that can be detected. In particular, after initial excitation of the fluorescent molecules 110 by the excitation light beam 106, the fluorescent molecules 110 emit light in different wavelengths. Once the fluorescent molecules 110 are initially excited, the fluorescent molecules 110 may then be illuminated again by the stimulation light beam 104 having a wavelength that the excited fluorescent molecule 110 may have emitted during initial excitation in order to reinforce light of that specific wavelength by the stimulated emission 108. However, the stimulated emission 108 generated by each fluorescent molecule 110 is difficult to distinguish from the stimulated light beam 104 since both travel along the same axis 300.

In some embodiments, the fluorescent molecules 110 may be fluorescent markers that are distributed in a sparse or non-uniform manner along the sample 102.

To distinguish and separate the stimulation light beam 104 from the stimulated emission 108, the fluorescence microscopy system 100 includes a stimulation light beam block component 112 associated with an objective lens 114 for effectively blocking the stimulation light beam 104 from detection by a detector 118 along axis 300. For example, the stimulation light beam block component 112 is positioned at the focal point of the objective lens 114 such that stimulation light beam 104 is focused onto the stimulation light beam block component 112 and blocked from detection by the detector 118, while allowing the stimulated emission 108 to be imaged around the stimulation light beam block component 112 and focused by a lens 116 onto the detector 118. In this arrangement, the fluorescence microscopy system 100 allows the stimulated emission 108 to be generated sooner by the fluorescent molecule 110 with the stimulated emission 108 having a particular desired wavelength.

In another embodiment, the fluorescence microscopy system, designated 200, also employs a technique for distinguishing stimulated emission as a means of enhancing signal strength of fluorescent markers is shown. In one arrangement, an excitation light beam 202 is generated by an excitation source 201 similar to the excitation source 101, which generates the excitation light beam 202 directed along a first axis 400 and is combined with a stimulation light beam 204 generated by a stimulation source 203 similar to stimulation source 103, which directs the stimulated light beam 204 along a second axis 402 that is in perpendicular relation to the first axis 400 to generate a combined excitation/stimulation light beam 205 at an intersection point 215 (represented in FIG. 2 as a circle). The combined excitation/stimulation light beam 205 generated by the intersection of the excitation light beam 202 with the stimulation light beam 204 at a perpendicular angle illuminates a sample 208 along second axis 402. In particular, the combined excitation/stimulation light beam 205 is captured by an excitation objective 216 that focuses the combined excitation/stimulation light beam 205 along the second axis 402 to illuminate the sample 208 in which one or more fluorescent molecules 210 (e.g. fluorescent markers) associated with the sample 208 are excited by the combined excitation/stimulation light beam 205. This excitation/stimulation of the sample 208 generates a stimulated emission 206 by the one or more fluorescent molecules 210 associated with the sample 208.

Figure 2:
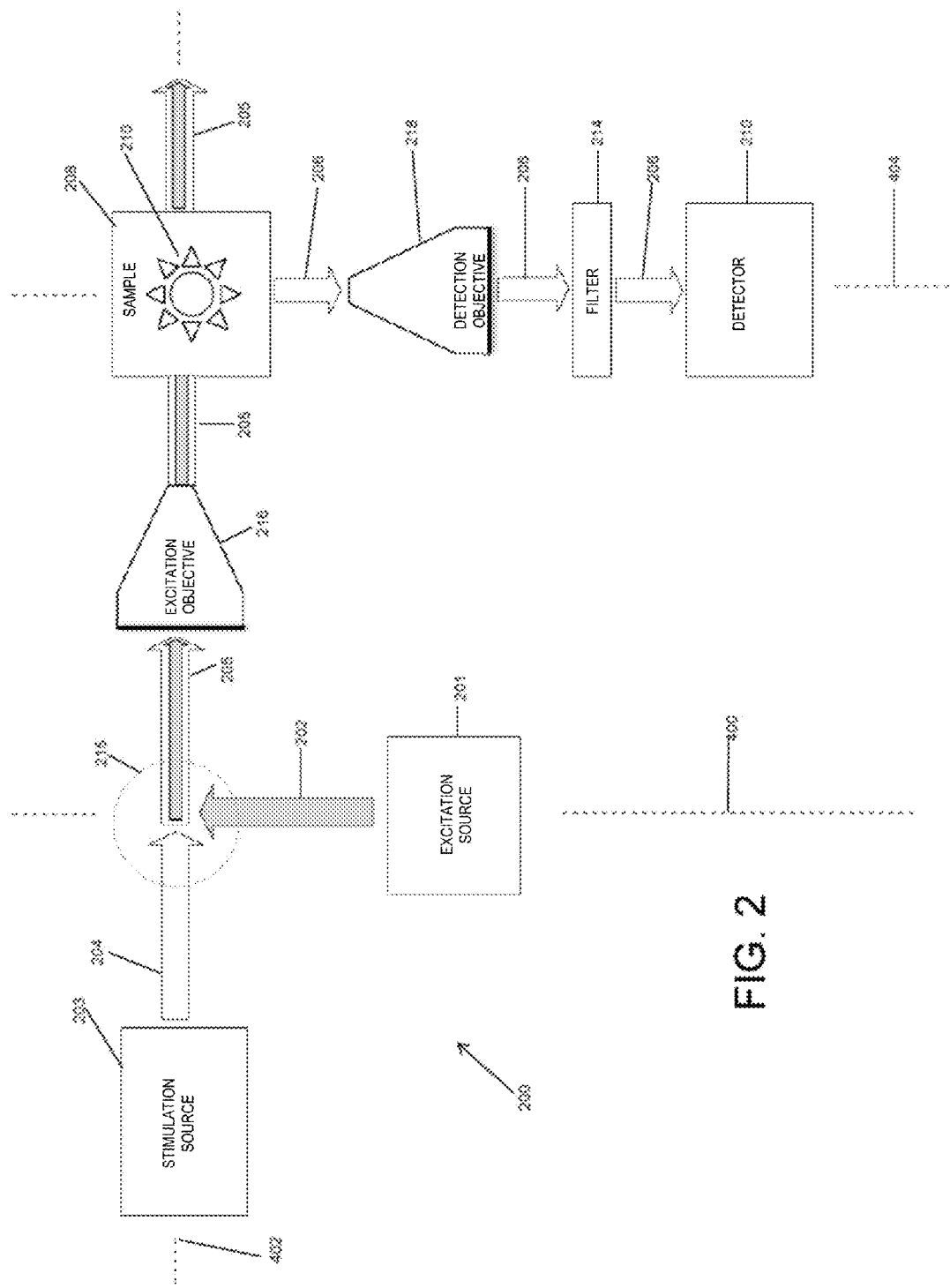
FIG. 2 is a simplified illustration of another embodiment of the fluorescence microscopy system.

Once the fluorescent molecules 210 are excited by the combined excitation/stimulation light beam 205, the combined excitation/stimulation light beam 205 continues along second axis 402 as shown in FIG. 2. A portion of the stimulated emission 206 is emitted in the direction of a third axis 404, which is in parallel orientation relative to the first axis 400 and in perpendicular orientation relative to the second axis 402, is captured by a detection objective lens 218. In one arrangement, the excitation objective lens 216 is in perpendicular orientation relative to the detection objective lens 218, which allows the stimulated emission 206 directed along third axis 404 to separate from the combined excitation/stimulation light beam 205 directed along second axis 402. As such, the fluorescence microscopy system 200 does not require the excitation objective lens 216 to include a stimulation light beam block component 112 of the fluorescence microscopy system 200 in order to separate the combined excitation/stimulation light beam 205 from the stimulated emission 206.

Once the stimulated emission 206 is captured by the detection objective lens 218, the stimulated emission 206 is focused onto a detector 210 for capturing images of the stimulated emission 206 emitted by the sample 208. In some embodiments, a filter 214 may be interposed between the detection objective 218 and the detector 210 in order to filter out portions of the stimulated emission 206.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A fluorescence microscopy system comprising:
   an excitation source for generating an excitation light beam along a first axis;
   a stimulation source for generating a stimulation light beam along a second axis that is in perpendicular orientation relative to the first axis, wherein the excitation light beam and the stimulation light beam have different wavelengths;
   a sample having one or more fluorescent markers which are illuminated by the excitation light beam such that the one or more fluorescent markers assumes an excited state and then illuminated again by the stimulation light beam to generate a stimulated emission by the initially excited sample;
   an objective lens oriented along the second axis for capturing and focusing the stimulation light beam and stimulated emission emitted by the one or more fluorescent markers;
   a stimulation light beam block component positioned at a focal point of the objective lens such that the stimulation light beam is blocked while allowing the stimulated emission to pass; and
   a detector for detecting the stimulated emission.

2. The fluorescence microscopy system of claim 1, wherein the excitation light beam along the first axis is not captured by the objective lens.

3. The fluorescence microscopy system of claim 1, wherein the stimulation light beam is collimated.

4. The fluorescence microscopy system of claim 1, further comprising:
   a lens in association with the objective lens for focusing the stimulated emission onto the detector.

5. The fluorescence microscopy system of claim 1, wherein the stimulated emission is imaged around the stimulation beam block component for detection by the detector.

6. The fluorescence microscopy system of claim 1, wherein the one or more fluorescence markers are distributed sparsely or in a non-uniform manner along the sample.

7. The fluorescence microscopy system of claim 1, wherein a wavelength of the stimulation emission is the same wavelength that the one or more fluorescent markers can emit during excitation of the sample by the excitation light beam.

8. The fluorescence microscopy system of claim 1, wherein the stimulation light beam has a wavelength of about 550 nm.

9. The fluorescence microscopy system of claim 1, wherein the stimulation source and the excitation source comprise a laser.

10. The fluorescence microscopy system of claim 1, wherein the excitation light beam has a wavelength of about 488 nm.

11. The fluorescence microscopy system of claim 1, wherein the stimulation light beam block component is aligned along the second axis and positioned to block the stimulated light beam from the objective lens.

12. A method for fluorescence microscopy comprising:
    illuminating one or more fluorescent markers in a sample with an excitation light beam from an excitation source oriented along a first axis such that the one or more fluorescent marker assume an excited state;
    illuminating the one or more fluorescent markers in the excited state with a stimulation light beam from a stimulation source oriented along a second axis that is in perpendicular relation to the first axis, wherein a stimulated emission is generated by the one or more fluorescent markers when illuminated by the stimulation light beam, wherein the stimulated light beam and the excitation light beam have different wavelengths;
    focusing the stimulation light beam and the stimulated emission through an objective lens;
    positioning a stimulated light beam block component along the second axis such that the stimulated light beam is focused onto and blocked by the stimulated light beam block component, and wherein the stimulated emission is not blocked by the positioning of the stimulated light beam block; and
    detecting the stimulated emission by a detector.

13. The method of claim 12, wherein the stimulated light beam block is positioned at a focal point of the objective lens and oriented along the second axis.

14. The method of claim 12, further comprising:
    focusing the stimulated emission using a lens onto the detector.

15. A fluorescence microscopy system comprising:
    an excitation source for generating an excitation light beam along a first axis;
    a stimulation source for generating a stimulation light beam along a second axis that is in perpendicular relation relative to the first axis, wherein the excitation light beam and the stimulation light beam have different wavelengths;
    a combined excitation/stimulation light beam that is generated by the intersection of the excitation light beam with the stimulation light beam;
    an excitation objective lens oriented along the first axis for capturing the combined excitation/stimulation light beam;
    a sample having one or more fluorescent markers in a focal plane of the excitation objective lens, wherein the one or more fluorescent markers are illuminated by the combined excitation/stimulation light beam for producing an stimulated emission;
    a detection objective lens oriented in perpendicular orientation relative to the excitation objective for capturing and focusing the stimulated emission emitted by the one or more fluorescent markers of the sample; and
    a detector for detecting the stimulated emission from the detection objective lens.

16. The fluorescence microscopy system of claim 15, further comprising:
    a filter in association with the detection objective lens for filtering the stimulated emission focused by the detection objective lens.

17. The fluorescence microscopy system of claim 15, wherein the wavelength of the stimulation emission is a wavelength that the one or more fluorescent markers can emit during excitation by the excitation light beam.

* * * * *